United States Patent [19]

Morel et al.

[11] Patent Number: 4,526,295

[45] Date of Patent: Jul. 2, 1985

[54] CARTRIDGE FOR INJECTING A SEMI-PASTY PRODUCT

[75] Inventors: André Morel; Jacques Morel, both of Chateauneuf-En-Thymerais, France

[73] Assignee: Etablissements Morelateliers Electromecanique De Favieres, Chateauneuf-En-Thymerais, France

[21] Appl. No.: 527,644

[22] PCT Filed: Dec. 8, 1982

[86] PCT No.: PCT/FR82/00204

§ 371 Date: Aug. 9, 1983

§ 102(e) Date: Aug. 9, 1983

[87] PCT Pub. No.: WO83/02103

PCT Pub. Date: Jun. 23, 1983

[30] Foreign Application Priority Data

Dec. 18, 1981 [FR] France ............................... 81 23670

[51] Int. Cl.³ ............................................. B65D 83/00
[52] U.S. Cl. ...................................... 222/82; 222/83; 222/137; 222/390; 174/84 R; 366/256
[58] Field of Search .................... 222/82, 83, 129, 136, 222/137, 386, 390; 174/84 R; 604/56, 87, 88, 89, 91, 184, 211, 224; 366/255, 256

[56] References Cited

U.S. PATENT DOCUMENTS

| | | | |
|---|---|---|---|
| 3,013,697 | 12/1961 | Gill | 222/390 X |
| 4,019,654 | 4/1977 | Van Manen | 222/390 X |
| 4,208,133 | 6/1980 | Korte-Jungermann | 222/137 X |
| 4,220,261 | 9/1980 | White | 222/320 X |
| 4,449,645 | 5/1984 | Korwin et al. | 222/390 X |

FOREIGN PATENT DOCUMENTS

| | | |
|---|---|---|
| 749096 | 7/1933 | France. |
| 1599814 | 7/1970 | France. |
| 2178733 | 11/1973 | France. |
| 2357311 | 2/1978 | France. |

Primary Examiner—Joseph J. Rolla
Assistant Examiner—Frederick R. Handren
Attorney, Agent, or Firm—Young & Thompson

[57] ABSTRACT

The injection cartridge comprises two containers (1, 2) one of which is slidably mounted in the other. An actuating rod (8) has a smooth leading portion (9) and a rear threaded portion (10) separated by a threaded intermediate portion (11). The container (1) has in its end (12) a threaded opening (13) receiving the threaded intermediate portion (11). The nozzle (5) of the container (2) has a thread (15) for receiving the thread (14). The threaded portion (10) of the rod (8) has a nut for abutting against the first container to push it towards the other container. The cartridge may be used for injecting a semi-pasty product into a protective sleeve for a joint in a telephone cable.

17 Claims, 24 Drawing Figures

FIG_5　　　FIG_6　　　FIG_7

FIG_10

FIG_12

FIG_11

FIG_13

FIG_14

CARTRIDGE FOR INJECTING A SEMI-PASTY PRODUCT

The present invention concerns a cartridge for injecting into a hollow body a semi-pasty product, such as a polyurethane foam obtained by mixing two constituents, namely a polyalcohol and an isocyanate.

By semi-pasty product is meant a product the viscosity of which is between 500 and 2,000 centipoise.

The cartridge proposed by the invention is intended, in particular, for injecting polyurethane foam into a sealing and electrically insulating sleeve surrounding the splice which joins electric or electronic cables.

There is known a cartridge for injecting a semi-pasty product obtained by mixing two constituents, comprising two containers, one container being slidably mounted in the other and each container containing one of the aforementioned constituents. One of the containers is separated from the other container by a partition wall.

The other container has a discharge nozzle for connection to the injection orifice of the hollow body. The partition wall of the first container and the discharge nozzle of the second container each have a closure pierceable by a perforating rod mounted axially in the cartridge.

The perforation of these closures enables respectively the passage of the first constituent into the second container and the passage of the resulting mixture through the discharge nozzle of the second container.

Experience has shown that the use of a cartridge of this type presented difficulties in the case of products having a viscosity greater than or equal to 1000 centipoise.

In fact, the injection of such products involves the exertion of considerable efforts to make the first container slide into the second container. It is therefore necessary to limit the dimensions of the cartridges and this requires the use of several cartridges to fill sleeves of large volume.

An object of the present invention is to eliminate these disadvantages by providing a cartridge which is easy to handle and capable of containing a volume of semi-pasty product considerably greater than that contained by conventional cartridges.

The injection cartridge proposed by the invention comprises two containers, one of which is slidably mounted in the other and each of which contains one of the two constituents of the mixture to be made up, one of the containers being separated from the other container by a partition wall, this other container having a discharge nozzle for connection to the injection orifice of the hollow body, the partition wall and the discharge nozzle each having a closure pierceable by a perforating rod mounted axially in the cartridge, to enable respectively the passage of the constituent from the first container into the second container and the passage of the resulting mixture through the discharge nozzle of the second container.

According to the invention, the cartridge is characterised in that the rod has a smooth leading portion and a threaded rear portion, the leading and rear portions being separated by a short threaded intermediate portion of larger diameter than the diameters of said leading and rear portions, that the first container has, in its end opposite to the second container, a threaded opening for receiving said threaded intermediate portion, that the free end of the smooth portion of the rod is threaded, that the discharge nozzle of the second container has an internal thread for receiving the thread provided on the end of this smooth portion, that the length of this smooth portion is greater than the distance between the partition wall and the thread of the first container, and that the threaded portion of the rod has a nut for abutting against the outside of the cartridge on the end of the first container, to push this latter into the second container.

The operation of the cartridge according to the invention as follows: The rod is inserted axially into the threaded opening of the first container. The threaded intermediate portion of the rod is screwed into this opening. During this operation, the end of the rod pierces the closure provided in the partition wall of this container. The first container thus communicates with the second container. The constituents contained in this container are mixed by making the first container slide several times, relative to the second container, in both directions.

The rod is then pushed further into the cartridge in order to screw the threaded end of the rod into the thread cut in the discharge nozzle of the second container. In this position, the threaded portion of the rod projects outside the threaded opening of the first container. The nut is screwed onto this threaded portion until it abuts on the adjacent end of the first container. Screwing of this nut is then continued, which causes the first container to be made to slide into the second container which, in turn, causes the product resulting from the mixture of the two constituents to be ejected through the discharge nozzle of the second container.

Use of the cartridge according to the invention is therefore particularly easy and does not require any special effort. A cartridge of this kind may be of large dimensions and this enables a hollow body of large volume to be filled in a single operation.

Other features and advantages of the invention will become apparent in the following description of embodiments of the invention, given by way of example with reference to the accompanying drawings.

In the first embodiment shown in the accompanying drawings, the cartridge for injecting into a hollow body a semi-pasty product such as polyurethane foam obtained by mixing a polyalcohol with an isocyanate, consists of two cylindrical containers 1, 2, of hard plastics material, one container being slidably mounted in the other and each container containing one of the aforementioned constituents.

Figure 1:
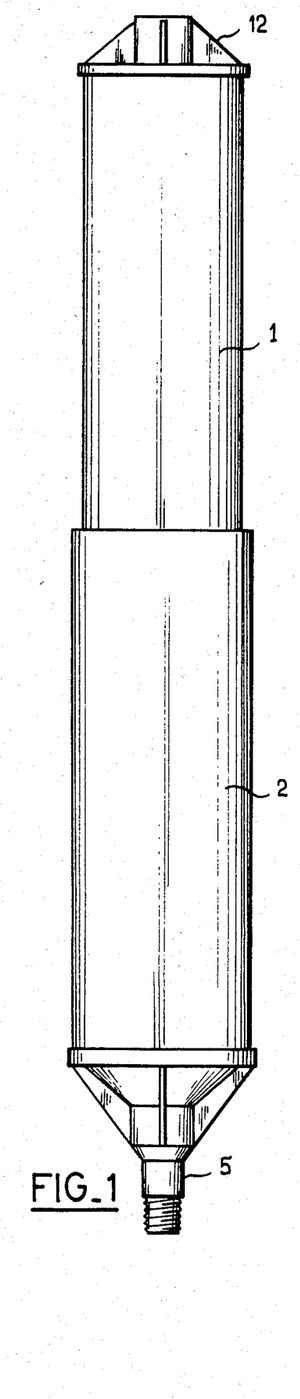
FIG. 1 is a plan view of a first embodiment of the cartridge according to the invention.
Figures 2, 3, 4:
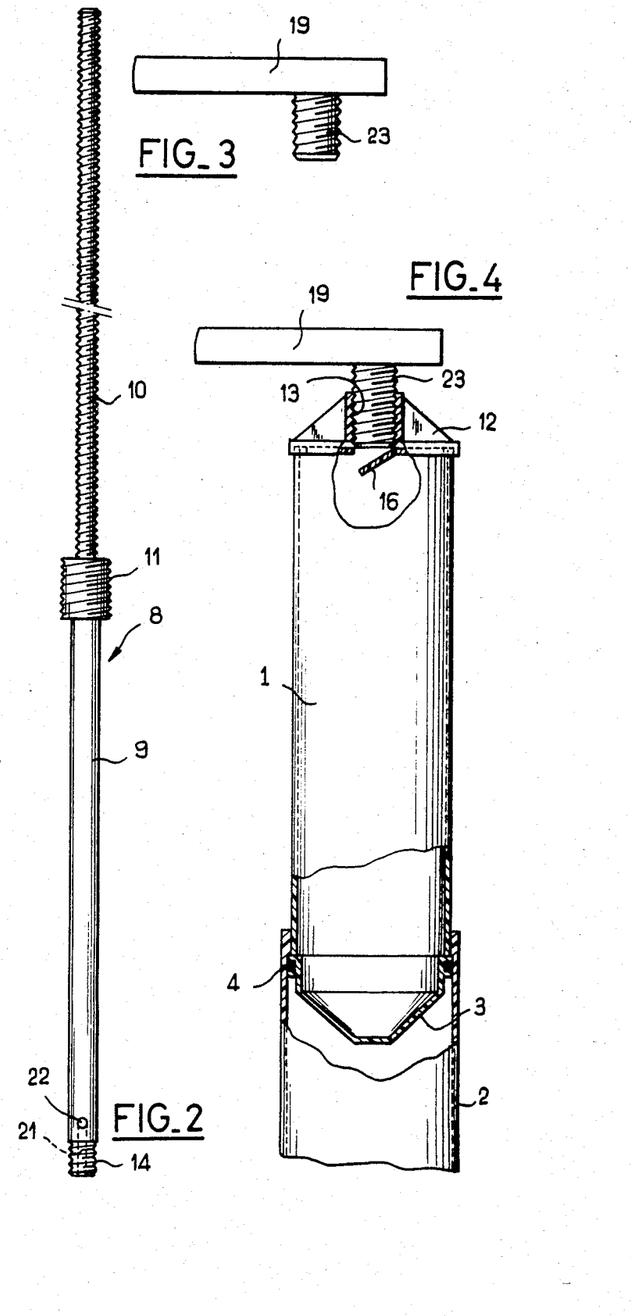
FIG. 2 is a plan view of the perforating rod of this cartridge.
FIG. 3 is a view of the nut for effecting the sliding of one of the containers into the other container of the cartridge.
FIG. 4 is a view of the cartridge in a part cut-away plan view, showing a preliminary phase of use of the cartridge.
Figures 5, 6, 7:
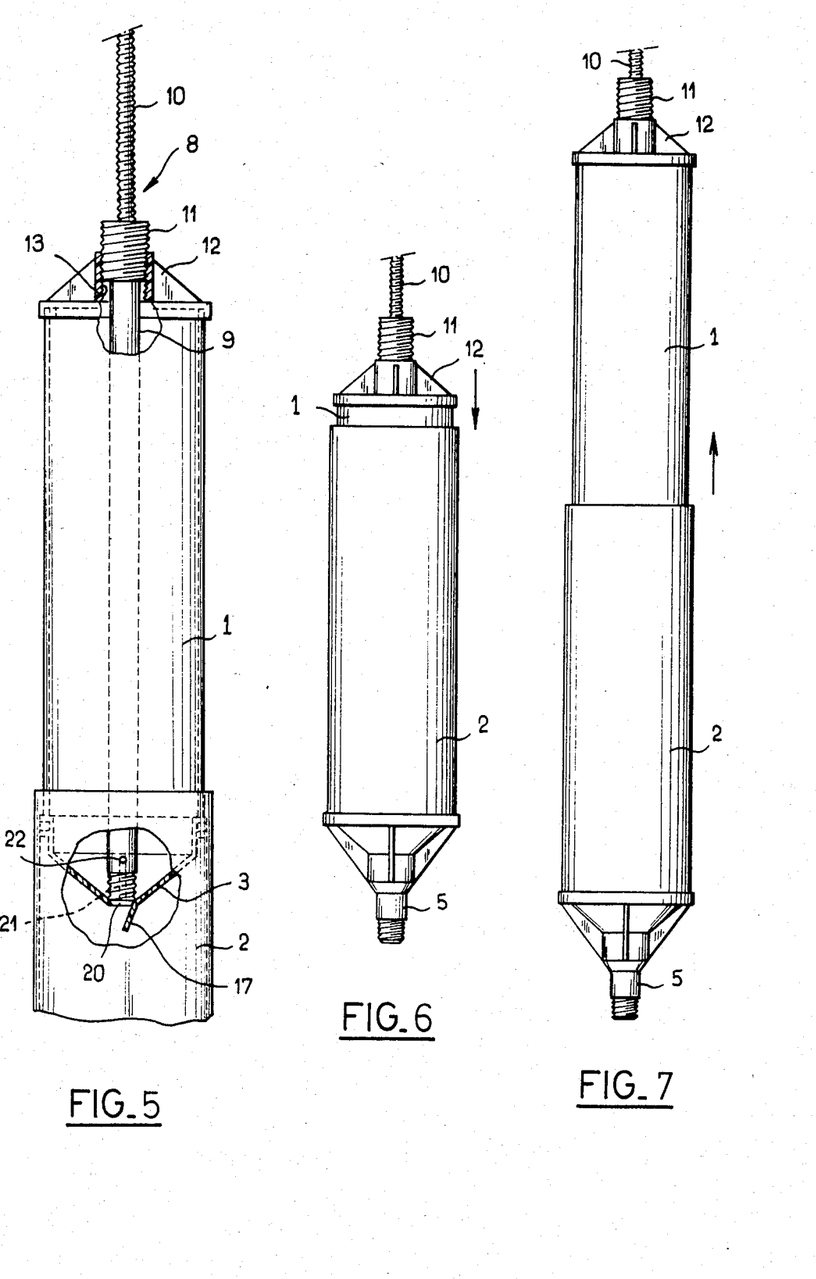
FIG. 5 is a view similar to FIG. 4, showing the next phase of use of the cartridge.
FIGS. 6 and 7 are plan views of the cartridge, the first container being respectively in a pressed-in position and a withdrawn position.
Figures 8, 9:
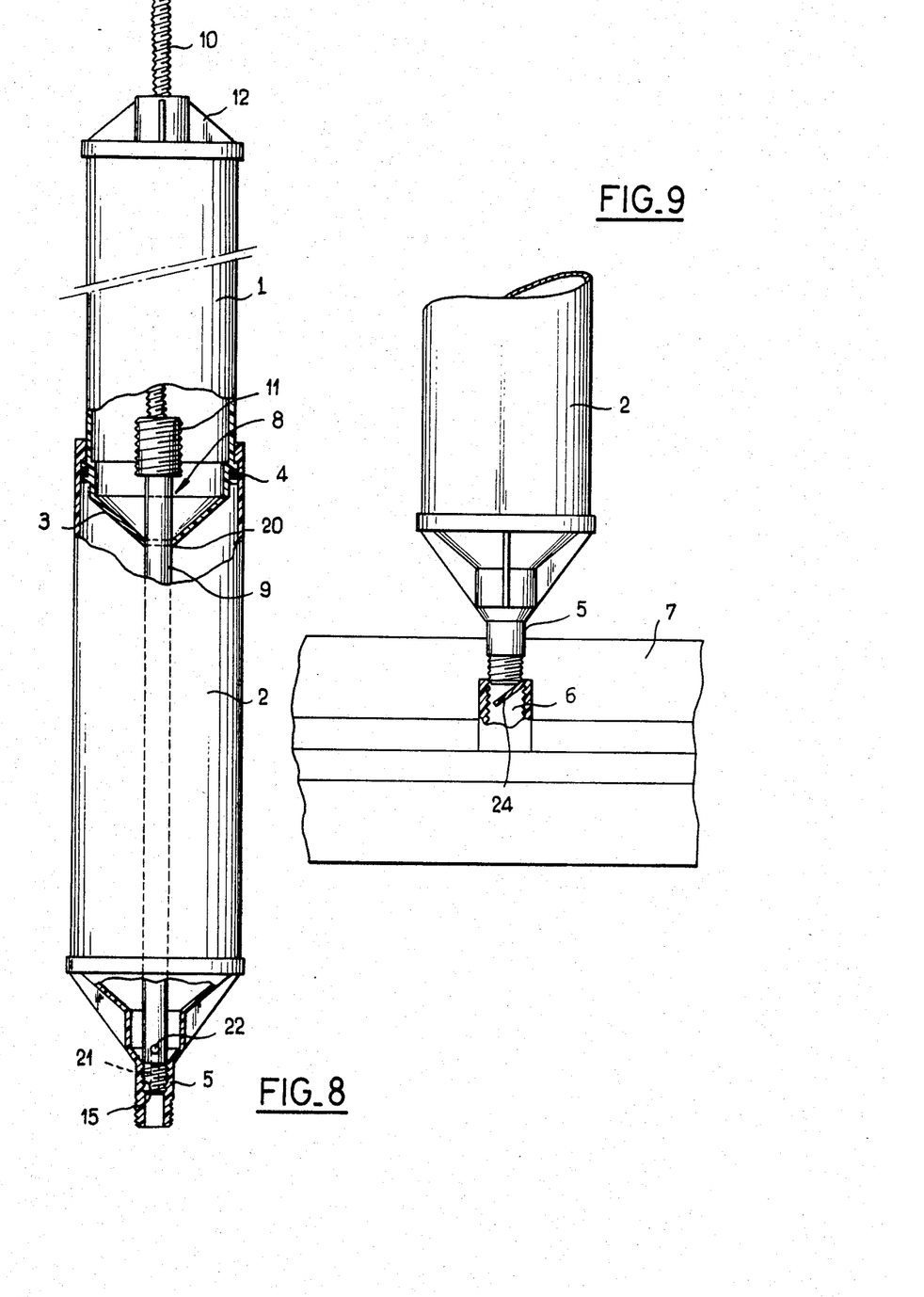
FIG. 8 is a part cut-away plan view of the cartridge, the end of the rod being in position, fixed in the discharge nozzle of the second container.
FIG. 9 is a view of the end of the cartridge, showing it being positioned on the injection orifice of a protective sleeve for telephone cables.

The end of the container 1 engaged in the container 2 is closed off by a substantially frusto-conical partition wall 3 (see FIGS. 4, 5 and 8). This end of the container 1 has a toroidal seal 4 which ensures leak-proof sealing between the two containers 1, 2.

Figure 10:
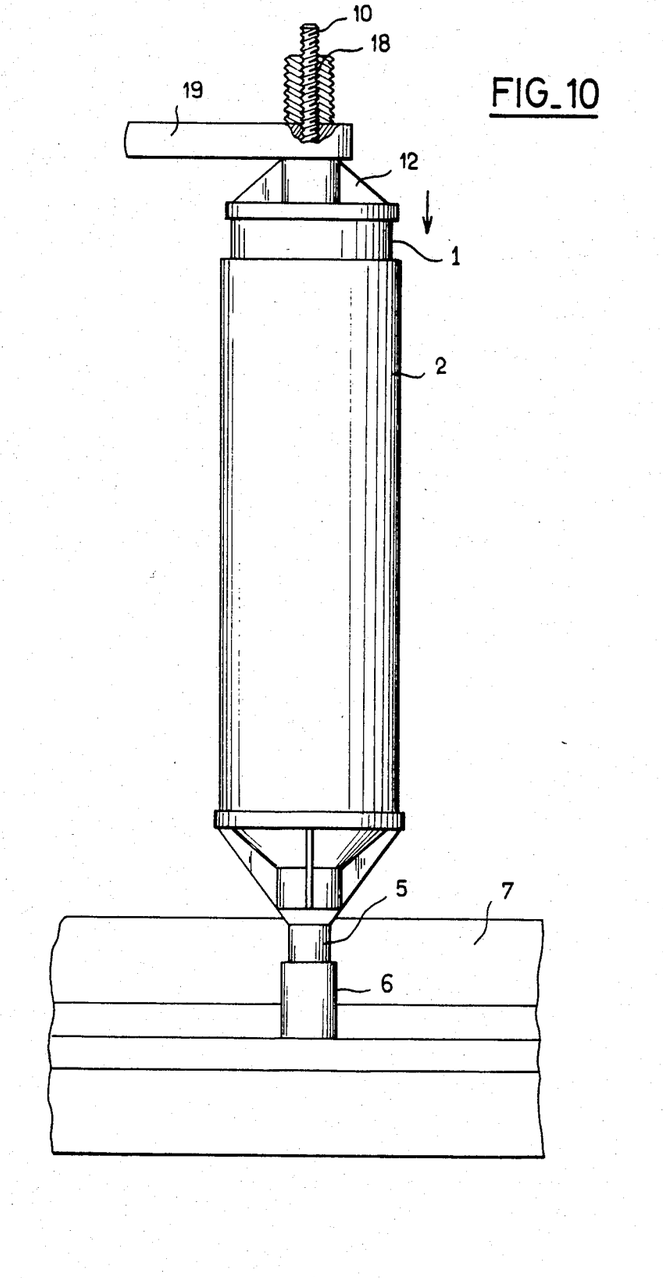
FIG. 10 is a plan view of the cartridge, showing the phase in which the product is injected into the sleeve, the operating nut being screwed onto the threaded portion of the rod.

At its opposite end from the container 1, the container 2 has a discharge nozzle 5 (see FIGS. 1 and 6 to 10), for connection to the injection orifice 6 of a protective sleeve 7 for a telephone cable (see FIGS. 9 and 10).

The cartridge also has a rod 8 (see in particular FIGS. 2 & 8), which has a leading smooth cylindrical portion 9 and a threaded rear portion 10. These portions 9 and 10 are separated by a short threaded intermediate portion 11, of larger diameter than that of the leading portion 9 or the rear portion 10.

The container 1 has a threaded axial opening 13 in its end 12 opposite to the container 2, for receiving the threaded intermediate portion 11 of the rod 8, as indicated in FIG. 5

The free end of the smooth portion 9 of the rod 8 has a screw-thread 14.

The discharge nozzle 5 of the container 2 has an internal screw-thread 15 (see FIG. 8) for receiving the screw thread 14 provided on the end of the rod 8.

The length of the smooth portion 9 of the rod 8 is slightly greater than the distance between the partition wall 3 of the container 1, and the thread 13 provided at the end 12 of this container 1 (see FIG. 5). This thread 13 has a closure 16 of plastics material for perforation or breaking-open, as indicated in FIG. 4. In addition, the partition wall 3 of the container 1 has a pierceable closure 17 (see FIG. 5). The thread 15 provided in the interior of the discharge nozzle 5 of the container 2 also has a perforatable closure which is not shown in the drawings.

The threaded portion 10 of the rod 8 has a nut 18 (see FIG. 10) provided with a lateral operating lever 19. In the position shown in FIG. 10, this nut 18 abuts against the end 12 of the container 1.

In FIG. 8, the opening 20 defined after perforation of the closure 17 provided in the partition wall 3 of the container 1, is seen to correspond to the section of the smooth portion 9 of the rod 8. Leak-proof sealing between this smooth portion 9 and the opening 20 is thus achieved.

In addition, the threaded end 14 of the rod 8 has a bore 21, (see FIGS. 2, 5 and 8) which opens laterally onto the smooth portion 9 through an orifice 22, the orifice permitting the passage of the product to be injected.

However, it is seen from FIGS. 3, 4 and 10 in particular, that the nut 18 with the lever 19 has an external thread 23 for screwing into the internal thread 13 provided at the end 12 of the container 1 in order to pierce the closure 16 located in this thread, as indicated in FIG. 4.

The operation of the cartridge just described will now be explained.

It will be assumed that the container 1 of the cartridge is filled with an isocyanate and that the container 2 contains a polyalcohol, these two constituents being intended to react together to form a polyurethane foam.

A preliminary operation consists of screwing the external thread 23 of the nut with the lever 19 into the internal thread 13 provided at the end 12 of the container 1. This operation causes the closure 16 (see FIG. 4) to be broken open.

The smooth portion 9 of the rod 8 is then inserted through the threaded opening 13 and the threaded intermediate portion 11 of this rod 8 is screwed into this threaded opening (see FIG. 5).

The threaded end 14 touches the closure 17 provided in the partition wall 3, and then breaks it open. The isocyanate then flows out into the lower container 2, by passing through the bore 21 provided in the end 14 of the rod 8.

The mixing of the isocyanate with the polyalcohol is speeded up by pressing the container 1 into the container 2, as indicated in FIG. 6, and then withdrawing it again, as indicated in FIG. 7. These two motions are carried out several times in order to achieve a homogeneous mixture between the two constituents. The two constituents react together to form a polyurethane foam, and this results in a considerable increase in pressure inside the container 2.

The rod 8 is then pressed into the container 2 and its threaded end 14 is screwed into the thread 15 provided in the nozzle 5 (see FIG. 8). The rod 8 is thus securely fixed in the nozzle 5. The nozzle 5 is then screwed (see FIG. 9) into the injection orifice 6 provided on the sleeve 7, and this causes the closure 24 provided in this orifice 6 to be broken open.

The nut 18 with the lever 19 is screwed (see FIG. 10) onto the projecting end of the threaded portion 10 of the rod 8 until this nut 18 abuts against the end 12 of the container 1. By continuing to screw the nut 18 by rotation of its lever 19, the container 1 is pressed into the container 2 and the opening 20 provided in the partition wall 3 of the container 1 slides in a sealing manner on the smooth portion 9 of the rod 8. The polyurethane foam is thus ejected gradually and without effort on the part of the user, through the bore 21 provided in the threaded end 14 of the rod 8.

Very viscous (viscosity greater than or equal to 1,000 centipoise) products can thus be ejected from the cartridge and in large quantity. A large-volume sleeve 7 can therefore be filled in a single operation, in conditions which are particularly convenient for the user.

Figure 15:
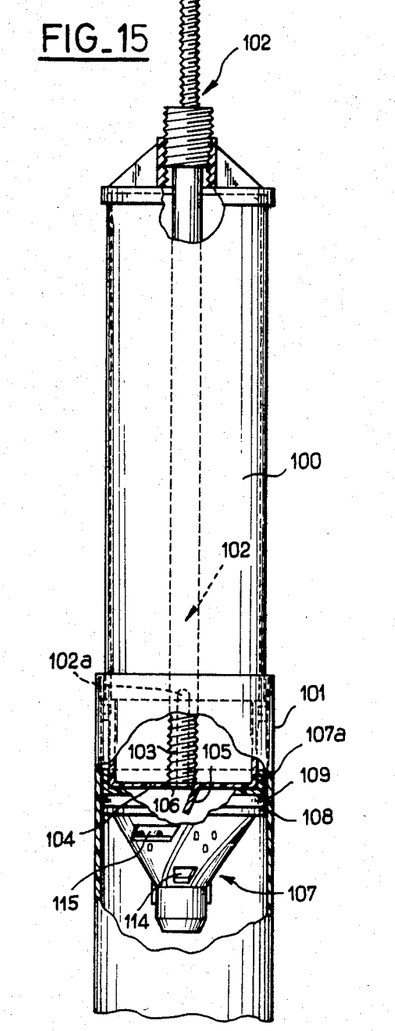
FIG. 15 is a part cut-away plan view of another embodiment of the cartridge according to the invention, showing the end of the rod piercing the partition wall of the first container.
Figure 16:
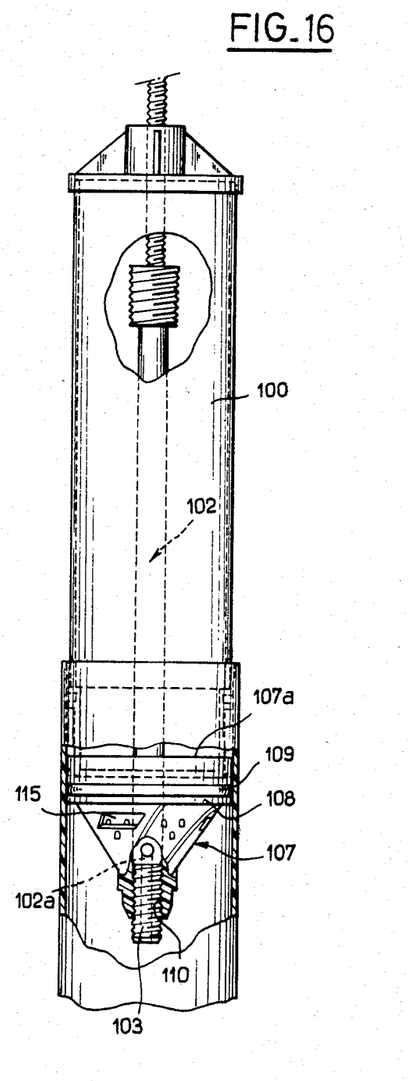
FIG. 16 is a view similar to FIG. 15, showing the end of the rod screwed into the piston.
Figures 17, 18, 19:
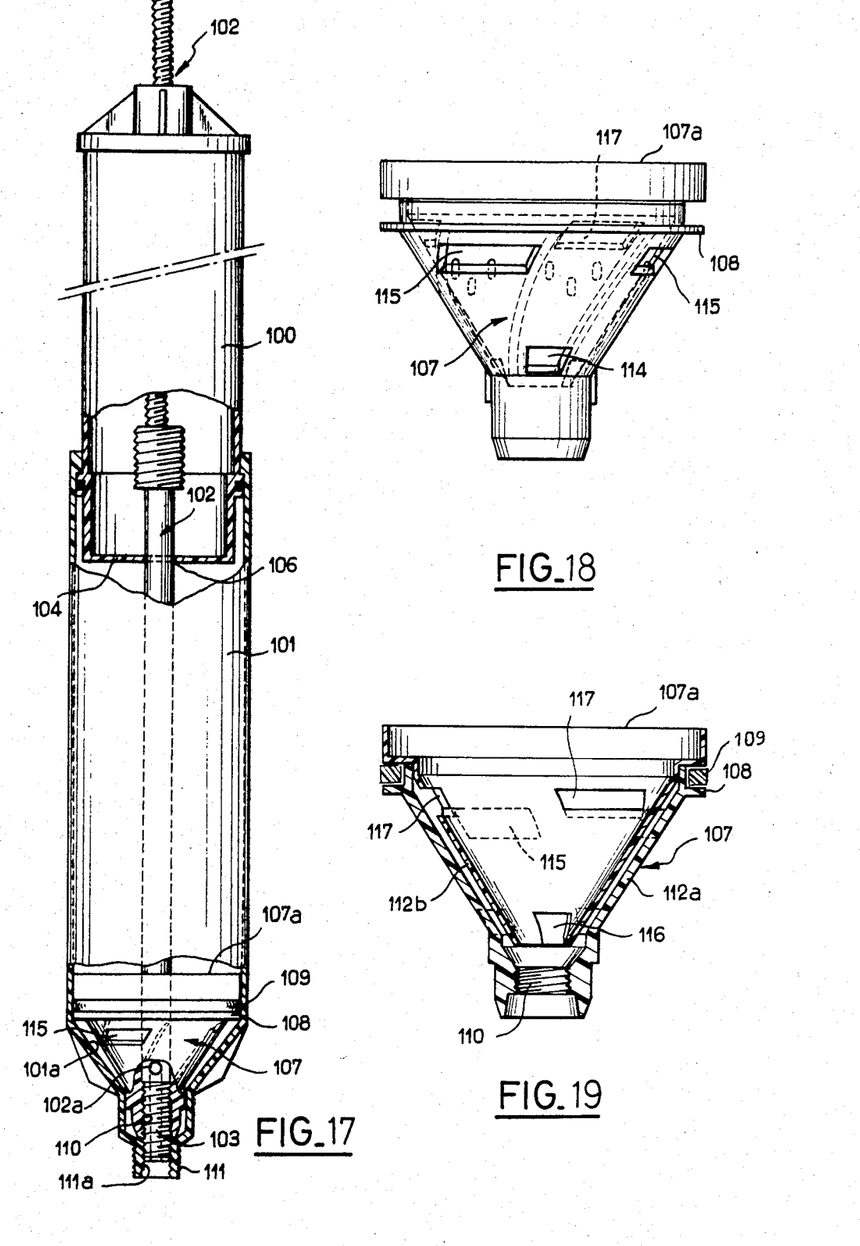
FIG. 17 is a view similar to FIG. 15, showing the piston near the discharge nozzle of the second container and the end of the rod screwed into this nozzle.
FIG. 18 is an elevation view of the piston on an enlarged scale.
FIG. 19 is a sectional view on the axis of the piston.

In the embodiment of FIGS. 15 to 17, the cartridge comprises two cylindrical containers 100 and 101, one slidably mounted in the other and each containing a constituent of the mixture to be made up and injected.

In the position shown in FIG. 15, a rod 102 is engaged axially in the first container 100. The threaded end 103 of this rod abuts against the partition wall 104 of the first container 100 and perforates the closure 105 of this partition wall, thus providing an orifice 106 in this latter.

The cartridge has a piston 107 mounted in a sliding manner in the second container 101. This piston 107 is substantially frusto-conical. Its outer frusto-conical surface is complementary to the internal frusto-conical surface 101a of the end of the container 101 adjacent to its threaded nozzle 111 (see FIG. 17).

In the position shown in FIG. 15, the base 107a of the piston 107 is received around the partition wall 104 and it has a flange 108 into which a ring 109 is inserted (see FIG. 19) in order to scrape the material along the inside wall of the container 101.

At its opposite end from the base 107a, the piston 107 has a threaded axial opening 110 able to receive the threaded end 103 of the rod 102, as indicated in FIG. 16.

This threaded end 103 of the rod 102 is of greater length than the threaded portion of the opening 110 of the piston 107, so that it can project outside this opening and can be screwed into the internal thread 111a of the discharge nozzle 111 of the second container 101 (see FIG. 17).

Figure 20:
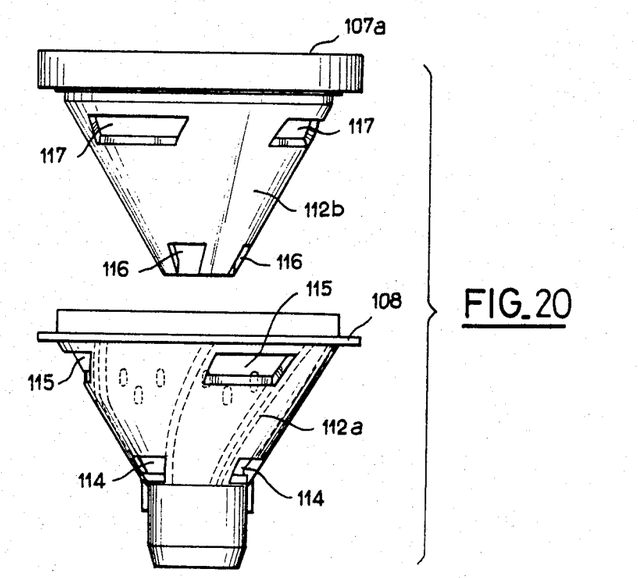
FIG. 20 is an exploded elevation of the piston, showing its two component parts.

It is seen from FIGS. 19 and 20 in particular that the piston 107 has two frusto-conical members 112a, 112b, axially assembled one inside the other in such a manner as to leave a space 113 between them. Each member 112a, 112b has two sets of openings 114, 115; 116, 117.

The largest openings 115, 117 are located near the base 107a of the piston and the smallest openings 114, 116 are located at the opposite end from this base.

In the embodiment shown, each set consists of three openings, distributed regularly over circles centered on the axis of the piston 107.

The openings 114 of the outer member 112a are displaced angularly with respect to the openings 115. Similarly, the openings 116 of the inner member 112b are displaced angularly relative to the openings 117.

In addition, the openings 114, 115 of the outer member 112a are displaced angularly with respect to the openings 116, 117 of the inner member 112b.

Figures 21, 22:
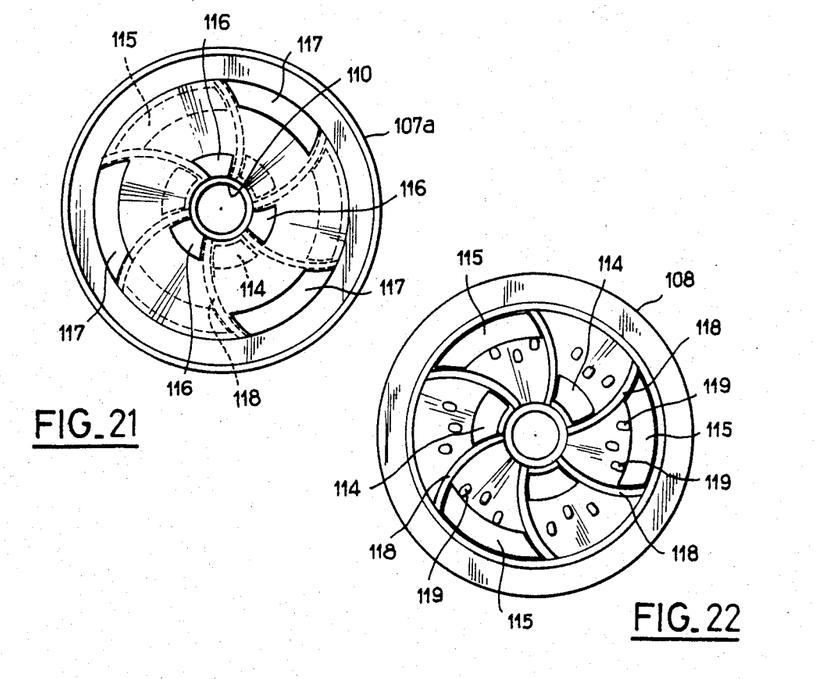
FIG. 21 is a plan view, showing the inside of the piston.
FIG. 22 is a plan view, showing the inside of the outer member of the piston.

The space 113 between the piston members 112a, 112b, is defined by curvilinear ribs 118 which extend over the internal face of the outer member 112a, between the central threaded orifice 110 and the flange 108 (see FIGS. 21 and 22). These curvilinear ribs 118 define, between the openings 114 of the outer member 112a and the openings 117 of the inner member 112b, on the one hand, and between the openings 116 of the inner member 112b and the openings 115 of the outer member 112a, on the other hand, passages extending along curvilinear paths, the section of which increases between the free end of the piston 107 and its base 107a.

It is also seen from FIG. 22 that the interior surface of the outer member 112a has protrusions 119 between the ribs 118.

The operation of the cartridge just described is as follows:

The rod 102 is inserted into the first container 100 and the closure 105 of the partition wall 104 is pierced (see FIG. 15). Communication is thus established between the two containers 100 and 101 through the internal bore 102a of the end 103 of the rod.

Pressing-in of the rod 102 is continued and its threaded end 103 is screwed into the threaded opening 110 provided in the end of the piston 107 (see FIG. 16).

The piston 107 is then displaced towards the end of the second container 101 and is then withdrawn again against the partition wall 104. This is repeated several times in succession.

Figure 23:
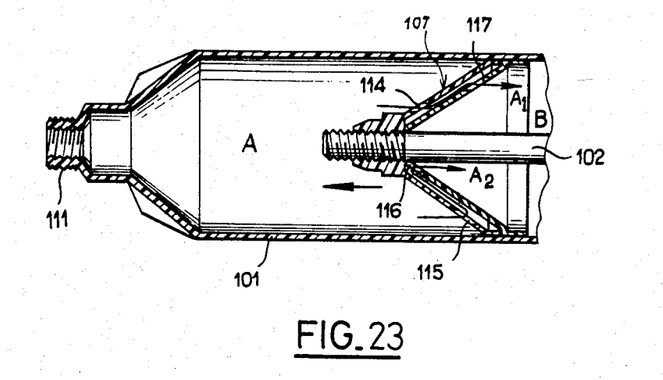
FIGS. 23 and 24 are diagrams illustrating the functioning of the second embodiment of the cartridge according to the invention.

When the piston 107 is displaced towards the end of the second container 101, the constituent A (see FIG. 23) contained in the container 101 enters into the piston 107 through the openings 114, passes into the curvilinear passages between the ribs 118 and emerges from these passages through the openings 117 (see arrow $A_1$ in FIG. 23). The constituent A is thus taken in near the axis of the container 101 and is then mixed with the constituent B in a region located at the periphery.

During this operation, the constituent A also enters into the piston 107 through the openings 115 and emerges from it through the openings 116 (see arrow $A_2$ in FIG. 23). The constituent A is thus likewise taken in at the periphery and then mixed with the constituent B in a region located near the axis.

When the piston is displaced rearwardly (see FIG. 24)—i.e. towards the first container 100, the constituent B contained in this enters into the piston 107 through the openings 117 and 116 and emerges from it through the openings 114 and 115 (see arrows $B_1$ and $B_2$).

Figure 24:
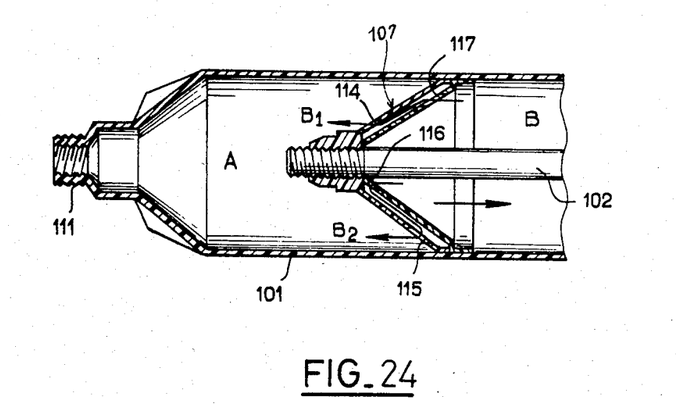

The constituent B is thus taken in near the axis and near the periphery of the container 101 and mixed with the constituent A in the regions located near the periphery and near the axis of the container respectively.

The protrusions 119 located in the passages between the aforementioned openings enable the flow of the material to be divided and this enables the homogenity of the mixture of the constituents A and B to be improved.

When the mixing of the constituents A and B has finished the threaded end 103 of the rod 102 is screwed into the thread of the nozzle 111, which causes the piston 107 to be applied against the internal frustoconical surface 101a of the end of the container 101.

The procedure as described above is then followed to inject the mixture obtained into a hollow body, such as a protective sleeve for telephone cables.

Obviously the present invention is not restricted to the embodiment just described and numerous modifications may be made to it without departing from the scope of the invention.

Thus, additional complementary sealing may be provided for the opening 20 of the partition wall 3 of the container 1.

The end 14 of the rod 8 may be arranged in such a way as to facilitate the piercing of different closures.

The cartridge according to the invention may also be used to inject semi-pasty products other than polyurethane foam and obtained by mixing at least two liquid and/or solid constituents.

Figure 11:
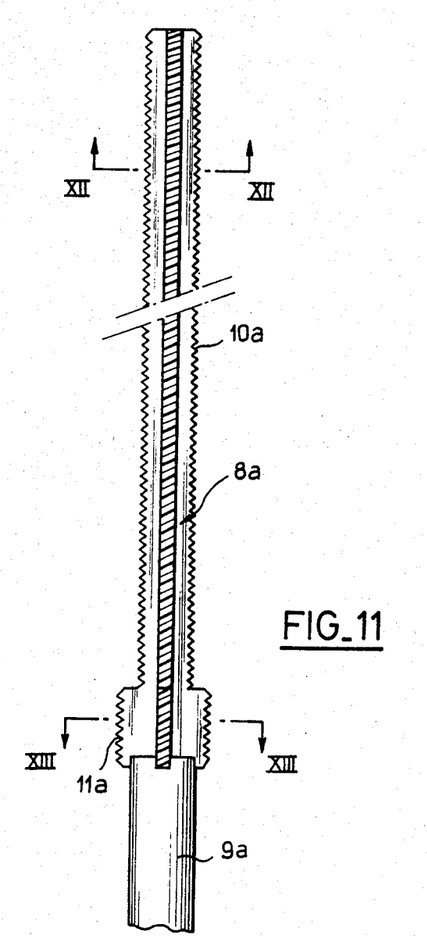
FIG. 11 is a partial view of another embodiment of the rod.
Figure 12:
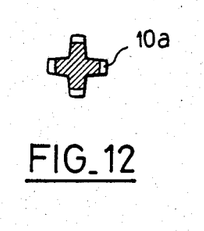
FIG. 12 is a sectional view on the line XII—XII of FIG. 11.
Figure 13:
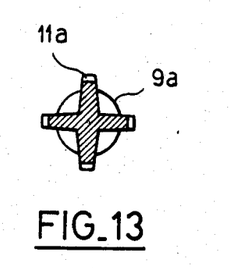
FIG. 13 is a sectional view on the line XIII—XIII of FIG. 11.

In the embodiment of FIGS. 11 to 13, the rear threaded portion 10a of the rod 8a has a star-shaped section with four points (see FIG. 12). The smooth leading portion 9a is identical with the region 9 of the rod 8 shown in FIG. 2. The threaded intermediate portion 11a also has a star-shaped section (see FIG. 13).

Figure 14:
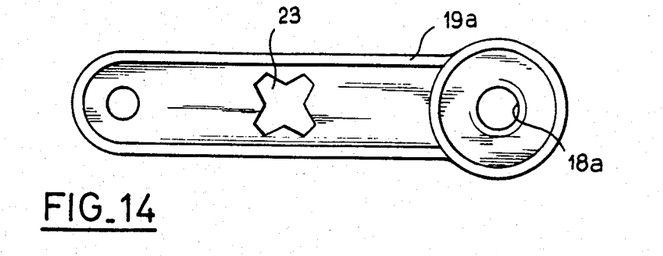
FIG. 14 is a plan view of an operating lever for the rod according to FIG. 11.

The lever 19a shown in FIG. 14 and carrying the nut 18a for screwing onto the threaded portion 10a of the rod 8a has an opening 23, the star-shaped section of which is adapted to the section of the threaded portion 10a of the rod 8a.

After introducing the rod 8a into the cartridge, the opening 23 of the lever is engaged on the threaded region 10a of the rod 8a. This lever greatly facilitates the rotation of the rod 8a when the closure 17 is being pierced.

Thus, the discharge nozzle 111 of the cartridge has an external thread enabling the cartridge to be screwed on to a fixed support, which would facilitate the handling of the cartridge during the operation of mixing the constituents A and B and would enable the semi-pasty product to be injected into a hollow body from a distance.

We claim:

1. A cartridge for injecting into a hollow body (7) a semi-pasty product obtained by mixing two constituents, comprising two containers (1, 2), one of which is slidably mounted in the other and each of which contains one of said two constituents, one of the containers being separated from the other container by a partition wall (3), the other container having a discharge nozzle (5) for connection to the injection orifice (6) of the hollow body, this partition wall (3) and the discharge nozzle (5) each having a closure (17) pierceable by a perforating rod (8) mounted axially in the cartridge, to enable respectively the passage of the constituent from the first container into the second container and the passage of the resulting mixture through the discharge nozzle of the second container, characterised in that the rod (8) has a smooth leading portion (9) and a threaded rear portion (10), the leading and rear portions being separated by a short threaded intermediate portion (11) of larger diameter than the diameters of said leading and rear portions, that a first said container (1) has in its end (12) opposite to a second said container (2), a threaded opening (13) for receiving said threaded intermediate portion (11), that the free end (14) of the smooth portion (9) of the rod is threaded, that the discharge nozzle (5) of the second container has an internal thread (15) for receiving the thread (14) provided on the end of the smooth portion, that the length of the smooth portion is greater than the distance between the partition wall (3) and the thread (13) of the first container, and that the threaded rear portion (10) of the rod (8) has a nut (18) for abutment against the outside of the cartridge, on the end (12) of the first container, to push this latter into the second container.

2. A cartridge according to claim 1, characterised in that the opening (20) defined after perforation of the closure (17) provided in the partition wall (3) of the first container (1) corresponds to the section of the smooth portion (9) of the rod (8).

3. A cartridge according to claim 1, characterised in that the threads (13, 15) provided in the end (12) of the first container (1) and in the discharge nozzle (5) of the second container (2) each have a closure (16) pierceable by means of the rod (8).

4. A cartridge according to claim 1, characterised in that the threaded end (14) of the smooth portion (9) of the rod (8) has a bore (21) which opens laterally on the smooth portion of the rod through an orifice (22) which permits the passage of the product to be injected.

5. A cartridge according to claim 3, characterised in that the nut (18) for mounting on the threaded rear portion (10) of the rod (8) has an external thread (23) for screwing into the thread (13) provided in the end of the first container (1) to pierce the closure (16) located in this thread.

6. A cartridge according to claim 1, characterised in that the nut (18) has a lever (19) for driving it in rotation.

7. A cartridge according to claim 1, characterised in that the rear threaded portion (10a) of the rod (8a) has a star-shaped section and that the lever (19a) for the nut (18a) has an opening (23) adapted to said section.

8. A cartridge according to claim 1, characterised in that it has a piston (107) slidably mounted in the second container (101), this piston having a threaded axial opening (110) enabling the threaded end (103) of the perforating rod (102) to be received, after the partition wall (104) of the first container (100) has been perforated by said end, that this threaded end of the rod (102) is of greater length than the threaded part of the axial opening (110) of the piston so that said threaded end may project out of this opening and may be screwed into the internal thread (110a) of the discharge nozzle (111) of the second container (101), and that the piston has a set of openings (114, 115, 116, 117) enabling the passage of the constituent contained in each container towards the other and vice versa, these openings being disposed in such a manner as to divert the path of the passage of the constituents from the axis of the second container (101) towards the periphery of said container when the piston (107) is displaced in one direction, and to divert said path from the periphery of the second container towards its axis when the piston is displaced in the other direction.

9. A cartridge according to claim 8, characterised in that the piston (107) is substantially frustoconical, its base (107a) adjacent to the partition wall of the first container (100) having a flange (108) in which an annular seal (109) is engaged to establish leak-proof sealing with the second container (101), that it has two frustoconical members (112a, 112b), axially asembled one inside the other in such a manner as to leave a space (113) between them, and that each member has two sets of openings (114, 115; 116, 117), one of these sets being located near the base (107a) of the piston and the other set being located at the opposite end from said base, and the openings of one of the members being displaced with respect to the openings of the other member.

10. A cartridge according to claim 9, characterised in that the two members (112a, 112b) of the piston (107) are separated by ribs (118) which define curvilinear paths for passage of the constituents.

11. A cartridge according to claim 10, characterised in that said curvilinear paths extend on the one hand, between the various openings (114) provided in the outer member (112a) at the opposite end from its base (107a) and the various openings (117), displaced relative to these, provided in the inner member (112b) near the base of the piston, and on the other hand, between the various openings (115) provided in the outer member (112a) near its base and the various openings (116), displaced with respect to these, provided in the inner member (112b) at the opposite end from its base.

12. A cartridge according to claim 11, characterised in that the openings (115, 117) located near the base of the piston (107) are larger than those located at the opposite end from this base.

13. A cartridge according to claim 9, characterised in that each member (112a, 112b) has two sets of three openings, distributed evenly over two separate circles centered on the axis of the piston (107).

14. A cartridge according to claim 9, characterised in that the external frustoconical surface of the piston (107) is complementary to the internal frustoconical surface (101a) of the end of the second container (101) adjacent to the discharge nozzle (111).

15. A cartridge according to claim 10, characterised in that the internal surface of one of the piston members is provided with protrusions (119) between the ribs (118) which define the curvilinear paths for passage of the constituents.

16. A cartridge according to claim 10, characterised in that the ribs (118) and the protrusions (119) are provided on the internal surface of the outer member (112a).

17. A cartridge according to claim 8, characterised in that the discharge nozzle (111) of the cartridge has an external thread enabling screwing of the nozzle onto a support.

* * * * *

UNITED STATES PATENT AND TRADEMARK OFFICE
CERTIFICATE OF CORRECTION

PATENT NO.  : 4,526,295
DATED       : July 2, 1985
INVENTOR(S) : Morel et al.

It is certified that error appears in the above—identified patent and that said Letters Patent is hereby corrected as shown below:

In the heading of the patent, under [30] Foreign Application Priority Data, insert the following:

--Sept. 24, 1982 [FR]  France ................82 16107--

Signed and Sealed this

Eighth Day of October 1985

[SEAL]

Attest:

Attesting Officer

DONALD J. QUIGG

Commissioner of Patents and Trademarks—Designate

UNITED STATES PATENT AND TRADEMARK OFFICE
CERTIFICATE OF CORRECTION

PATENT NO. : 4,526,295
DATED       : July 2, 1985
INVENTOR(S) : Andre MOREL et al.

It is certified that error appears in the above—identified patent and that said Letters Patent is hereby corrected as shown below:

In the name of the assignee, change "Morelateliers" to

--Morel - Ateliers--.

*Signed and Sealed this*

*Seventeenth* Day of *December 1985*

[SEAL]

*Attest:*

DONALD J. QUIGG

*Attesting Officer*    *Commissioner of Patents and Trademarks*